United States Patent [19]

Shimoda et al.

[11] Patent Number: 5,595,852
[45] Date of Patent: Jan. 21, 1997

[54] ORGANOSILICON COMPOUND, PRODUCING METHOD THEREOF AND TONER AND DRY-TYPE DEVELOPER USING THE SAME

[75] Inventors: Masakatsu Shimoda, Higashikurume; Haruo Iimura, Yamato; Hiroyuki Takahashi, Yokohama; Fuyuhiko Matsumoto, Yamato, all of Japan

[73] Assignee: Ricoh Company, Ltd., Tokyo, Japan

[21] Appl. No.: 534,640

[22] Filed: Sep. 27, 1995

[30] Foreign Application Priority Data

| Sep. 29, 1994 | [JP] | Japan | 6-234571 |
| Jan. 26, 1995 | [JP] | Japan | 7-030018 |
| Mar. 31, 1995 | [JP] | Japan | 7-076641 |
| Mar. 31, 1995 | [JP] | Japan | 7-076826 |
| Sep. 11, 1995 | [JP] | Japan | 7-233135 |
| Sep. 12, 1995 | [JP] | Japan | 7-234526 |
| Sep. 27, 1995 | [JP] | Japan | 7-273603 |

[51] Int. Cl.$^6$ .................................................. G03G 9/097
[52] U.S. Cl. .............................................................. 430/110
[58] Field of Search .................................................. 430/110

[56] References Cited

U.S. PATENT DOCUMENTS

| 4,902,570 | 2/1990 | Heinemann et al. | 430/110 |
| 4,973,540 | 11/1990 | Machida et al. | 430/110 |
| 5,021,317 | 6/1991 | Matsubara et al. | 430/110 |
| 5,188,929 | 2/1993 | Ishii | 430/110 |

*Primary Examiner*—Roland Martin
*Attorney, Agent, or Firm*—Cooper & Dunham LLP

[57] ABSTRACT

There are provided an organosilicon compound of formula (I) and a producing method thereof:

$$[R^2-\underset{\underset{R^3}{|}}{\overset{\overset{R^1}{|}}{Si}}CH_2CH_2CH_2NMe_2R^4]^+X^- \quad (I)$$

wherein $R^1$, $R^2$ and $R^3$ each is an alkyl group having 1 to 6 carbon atoms, or a phenyl group which may have a substituent; $R^4$ is an alkyl group which may have a substituent, an alicyclic alkyl group, a phenyl group which may have a substituent, or a benzyl group which may have a substituent; and X is a halogen atom, a benzenesulfonate radical, a hydroxynaphthalenesulfonate radical, $BPh_4$, $BF_4$, $ClO_4$, or $SbCl_5$. In addition, a toner and a two-component dry developer for developing latent electrostatic images containing the above organosilicon compound are also provided.

18 Claims, No Drawings

ORGANOSILICON COMPOUND, PRODUCING METHOD THEREOF AND TONER AND DRY-TYPE DEVELOPER USING THE SAME

BACKGROUND OF THE INVENTION

1. Field of the Invention

The present invention relates to an organosilicon compound and the method of producing such an organosilicon compound. In addition, the present invention also relates to a toner and a dry developer comprising the above-mentioned organosilicon compound for developing latent electrostatic images formed by an electrophotographic process.

2. Discussion of Background

To make a copy by the electrophotographic process, there is conventionally well known a method of uniformly charging a photoconductor, exposing the thus charged photoconductor to light images based on an original document to dissipate the electric charge of the light-exposed areas on the photoconductor, thereby forming latent electrostatic images corresponding to the light images, and then developing the latent electrostatic images into visible images by a two-component dry developer comprising carrier particles and toner particles. In such a two-component dry developer fine toner particles are held on the surface of a relatively large carrier particle triboelectrically, that is, by means of electrostatic force generated by the friction between both particles. When the carrier particle covered with toner particles is brought into immediate proximity of the latent electrostatic image, the electrostatic forces of the latent electrostatic image attracting the toner particles overcome the carrier-toner bond, and the toner particles are attracted to the latent electrostatic image and deposited thereon. Thus, latent electrostatic images can be developed into visible images.

The requirements for such toner particles are excellent chargeability, minimum moisture-absorption characteristics, good stability for an extended period of time, and proper fluidity. Of these requirements, the chargeability, the moisture-absorption characteristics and the stability are much influenced by a charge controlling agent contained in the toner particles.

The charge controlling agent, which is added to a formulation for a toner in order to impart a required charge quantity to the toner, is one of the very important materials constituting the toner. Depending on the desired properties of a developer to be obtained, the toner is positively or negatively charged by a positively or negatively chargeable charge controlling agent.

Examples of the conventional charge controlling agent capable of negatively charging the toner include metal complexes such as Cr- and Co-complexes (as disclosed in Japanese Laid-Open Patent Applications 61-217061 and 63-216061), nitrohumic acids (as disclosed in Japanese Laid-Open Patent Application 50-133838), and phthalocyanine pigment (as disclosed in Japanese Laid-Open Patent Application 60-258560).

Examples of the conventional charge controlling agent capable of positively charging the toner include salts of a nigrosine dye (as disclosed in Japanese Laid-Open Patent Application 56-22441), a variety of quaternary ammonium salts (as disclosed in Japanese Laid-Open Patent Application 59-136747), and imidazole derivatives (as disclosed in Japanese Laid-Open Patent Application 3-72373).

The conventional toners employing the above-mentioned conventional charge controlling agents did not meet all of the above-mentioned requirements such as excellent chargeability, minimum moisture-absorption characteristics and good stability. In addition, the compatibility of each conventional charge controlling agent with a binder agent is poor.

For instance, although a toner comprising a conventional nigrosine dye as the positively chargeable charge controlling agent shows a relatively high chargeability, the adhesion of the toner to a base material such as a sheet of paper is very poor. Further, the conventional nigrosine dye assumes a black color, so that the application of such a charge controlling agent is limited from the viewpoint of the hue of the toner to be obtained. Some toners employing the conventional quaternary ammonium salts as the charge controlling agents have the shortcoming that the moisture absorption is considerably high, so that the stability of the toners cannot be ensured for an extended period of time, and it becomes difficult to repeatedly obtain images using such toners.

SUMMARY OF THE INVENTION

It is therefore a first object of the present invention to provide an organosilicon compound which is capable of exhibiting charge controlling performance and good compatibility with a resin when used in a toner for developing latent electrostatic images.

A second object of the present invention is to provide a method of producing the above-mentioned organosilicon compound.

A third object of the present invention is to provide a toner for developing latent electrostatic images free from the conventional shortcomings, provided with good chargeability, minimum moisture-absorption characteristics, and high stability.

A fourth object of the present invention is to provide a two-component dry developer for developing latent electrostatic images comprising the above-mentioned toner component.

The first object of the present invention can be achieved by an organosilicon compound of formula (I):

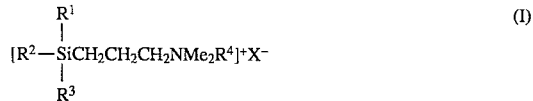

wherein $R^1$, $R^2$ and $R^3$ each is an alkyl group having 1 to 6 carbon atoms, or a phenyl group which may have a substituent; $R^4$ is an alkyl group which may have a substituent, an alicyclic alkyl group, a phenyl group which may have a substituent, or a benzyl group which may have a substituent; and X is a halogen atom, a benzenesulfonate radical, a hydroxynaphthalenesulfonate radical, $BPh_4$, $BF_4$, $ClO_4$, or $SbCl_5$.

The second object of the present invention can be achieved by a method of producing an organosilicon compound of formula (I) comprising the step of converting 3-N,N-dimethylaminopropylsilane of formula (II) to a quaternary salt by use of a quaternarization agent:

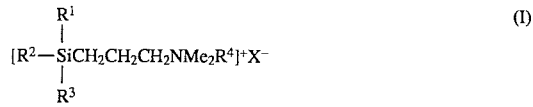

wherein $R^1$, $R^2$ and $R^3$ each is an alkyl group having 1 to 6 carbon atoms, or a phenyl group which may have a substituent; $R^4$ is an alkyl group which may have a substituent, an alicyclic alkyl group, a phenyl group which may have a substituent, or a benzyl group which may have a substituent; and X is a halogen atom, a benzenesulfonate radical, a hydroxynaphthalenesulfonate radical, $BPh_4$, $BF_4$, $ClO_4$, or $SbCl_5$; and $$R^2-\underset{R^3}{\underset{|}{Si}}CH_2CH_2CH_2NMe_2 \quad \text{(II)}$$
$$\overset{R^1}{|}$$

wherein $R^1$, $R^2$ and $R^3$ each is an alkyl group having 1 to 6 carbon atoms, or a phenyl group which may have a substituent.

The third object of the present invention can be achieved by a toner for developing latent electrostatic images comprising toner particles which comprise a resin, a coloring agent, and an organosilicon compound of formula (I):

$$[R^2-\underset{R^3}{\underset{|}{Si}}CH_2CH_2CH_2NMe_2R^4]^+X^- \quad \text{(I)}$$
$$\overset{R^1}{|}$$

wherein $R^1$, $R^2$ and $R^3$ each is an alkyl group having 1 to 6 carbon atoms, or a phenyl group which may have a substituent; $R^4$ is an alkyl group which may have a substituent, an alicyclic alkyl group, a phenyl group which may have a substituent, or a benzyl group which may have a substituent; and X is a halogen atom, a benzenesulfonate radical, a hydroxynaphthalenesulfonate radical, $BPh_4$, $BF_4$, $ClO_4$, or $SbCl_5$.

In the above-mentioned toner, it is preferable that the organosilicon compound of formula (I) be contained in an amount ranging from 0.5 to 30 parts by weight, more preferably 1 to 10 parts by weight, to 100 parts by weight of the resin.

The fourth object of the present invention can be achieved by a dry developer for developing latent electrostatic images comprising a toner which comprises toner particles comprising a resin, a coloring agent and an organosilicon compound of formula (I):

$$[R^2-\underset{R^3}{\underset{|}{Si}}CH_2CH_2CH_2NMe_2R^4]^+X^- \quad \text{(I)}$$
$$\overset{R^1}{|}$$

wherein $R^1$, $R^2$ and $R^3$ each is an alkyl group having 1 to 6 carbon atoms, or a phenyl group which may have a substituent; $R^4$ is an alkyl group which may have a substituent, an alicyclic alkyl group, a phenyl group which may have a substituent, or a benzyl group which may have a substituent; and X is a halogen atom, a benzenesulfonate radical, a hydroxynaphthalenesulfonate radical, $BPh_4$, $BF_4$, $ClO_4$, or $SbCl_5$; and a carrier.

DESCRIPTION OF THE PREFERRED EMBODIMENTS

Although the organosilicon compound is utilized in various fields, the application to the field of a developer for use in electrophotography is extremely limited to some cases. For example, there is proposed a toner comprising an additive component treated with a silane coupling agent as disclosed in Japanese Laid-Open Patent Application 5-66601; and there is proposed a developer which comprises a binder resin having a pendant with silicon substituent as disclosed in Japanese Laid-Open Patent Application 4-251865. The organosilicon compound has never been employed as a charge controlling agent for use in the toner.

The inventors of the present invention have succeeded in synthesizing various organosilicon compounds, and found by intensive evaluation that an organosilicon compound represented by the following formula (I) can be easily synthesized, and has the advantages of high thermal stability, minimum moisture-absorption characteristics, and good charging properties:

$$[R^2-\underset{R^3}{\underset{|}{Si}}CH_2CH_2CH_2NMe_2R^4]^+X^- \quad \text{(I)}$$
$$\overset{R^1}{|}$$

wherein $R^1$, $R^2$ and $R^3$ each is an alkyl group having 1 to 6 carbon atoms, or a phenyl group which may have a substituent; $R^4$ is an alkyl group which may have a substituent, an alicyclic alkyl group, a phenyl group which may have a substituent, or a benzyl group which may have a substituent; and X is a halogen atom, a benzenesulfonate radical, a hydroxynaphthalenesulfonate radical, $BPh_4$, $BF_4$, $ClO_4$, or $SbCl_5$.

The above-mentioned organosilicon compound of formula (I) can be prepared by converting 3-N,N-dimethylaminopropyl silane of the following formula (II) to a quaternary salt by use of a quaternarization agent in an organic solvent such as acetone, diethyl ether or tetrahydrofuran:

$$R^2-\underset{R^3}{\underset{|}{Si}}CH_2CH_2CH_2NMe_2 \quad \text{(II)}$$
$$\overset{R^1}{|}$$

wherein $R^1$, $R^2$ and $R^3$ each is an alkyl group having 1 to 6 carbon atoms, or a phenyl group which may have a substituent.

The above-mentioned 3-N,N-dimethylaminopropyl silane of formula (II) can be prepared by a so-called hydrosilylation reaction, namely, by allowing hydrosilane of formula (III) to react with N,N-dimethylallylamine of formula (IV) in isopropyl alcohol in the presence of a catalyst of chloroplatinic acid:

$$R^2-\underset{R^3}{\underset{|}{Si}}-H \quad \text{(III)}$$
$$\overset{R^1}{|}$$

wherein $R^1$, $R^2$ and $R^3$ each is an alkyl group having 1 to 6 carbon atoms, or a phenyl group which may have a substituent; and $$CH_2=CHCH_2NMe_2 \quad \text{(IV).}$$

Of the 3-N,N-dimethylaminopropyl silane compounds represented by formula (II), 3-N,N-dimethylaminopropyl trimethylsilane of formula (V) can be prepared by allowing chlorotrimethyl silane of formula (VI) to react with N,N-dimethylaminopropyl magnesium chloride of formula (VII) in tetrahydrofuran:

$$Me_3SiCH_2CH_2CH_2NMe_2 \quad \text{(V),}$$

$$Me_3SiCl \quad \text{(VI)}$$

and $$ClMgCH_2CH_2CH_2NMe_2 \quad \text{(VII).}$$

Examples of the alkyl group represented by $R^1$ to $R^4$ in formulae (I), (II) and (III) include methyl group, ethyl group, propyl group, butyl group, pentyl group and hexyl group.

Examples of the substituent of the phenyl group represented by $R^1$ to $R^3$ in formulae (I), (II) and (III) include an amino group substituted with at least one alkyl group having 1 to 4 carbon atoms, nitro group, and cyano group.

The substituent of the alkyl group represented by $R^4$ in formula (I) is a halogen atom such as chlorine or bromine.

As the alicyclic alkyl group represented by $R^4$ in formula (I), cyclohexyl group can be employed.

Examples of the substituent of the phenyl group represented by $R^4$ in formula (I) include a halogen atom, an alkyl group having 1 to 4 carbon atoms, and an alkoxyl group having 1 to 4 carbon atoms.

Examples of the substituent of the benzyl group represented by $R^4$ in formula (I) include a halogen atom, an alkyl group having 1 to 4 carbon atoms, and an alkoxyl group having 1 to 4 carbon atoms.

Specific examples of the organosilicon compound of formula (I) according to the present invention are shown below, but the examples are not limited to the following compounds. In the following chemical formulae, Me denotes methyl group; Et, ethyl group; nPr, n-propyl group; nBu, n-butyl group; cHex, cyclohexyl group; nHex, n-hexyl group; and Benz, benzyl group.

No. 1 $[Ph_3SiCH_2CH_2CH_2NMe_3]^+$ $I^-$
No. 2 $[Ph_3SiCH_2CH_2CH_2NMe_3]^+$ $Br^-$
No. 3 $[Ph_3SiCH_2CH_2CH_2NMe_2Et]^+$ $I^-$
No. 4 $[Ph_3SiCH_2CH_2CH_2NMe_2nPr]^+$ $I^-$
No. 5 $[Ph_3SiCH_2CH_2CH_2NMe_2nBu]^+$ $I^-$
No. 6 $[Ph_3SiCH_2CH_2CH_2NMe_2nBu]^+$ $Br^-$
No. 7 $[Ph_3SiCH_2CH_2CH_2NMe_2nHex]^+$ $I^-$
No. 8 $[Ph_3SiCH_2CH_2CH_2NMe_2cHex]^+$ $I^-$
No. 9 $[Ph_3SiCH_2CH_2CH_2NMe_2Benz]^+$ $I^-$
  (Benz=$CH_2Ph$)
No. 10 $[Ph_3SiCH_2CH_2CH_2NMe_2Benz]^+$ $Br^-$
No. 11 $[Ph_3SiCH_2CH_2CH_2NMe_2nPr]^+$ $I^-$

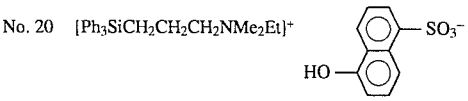

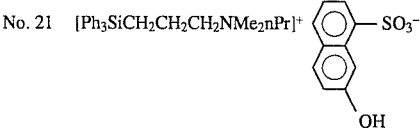

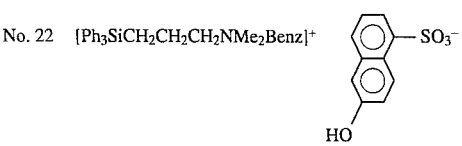

No. 23 $[Ph_3SiCH_2CH_2CH_2NMe_3]^+$ $BPh_4^-$
No. 24 $[Ph_3SiCH_2CH_2CH_2NMe_2nBu]^+$ $BPh_4^-$
No. 25 $[Ph_3SiCH_2CH_2CH_2NMe_2Et]^+$ $BF_4^-$
No. 26 $[Ph_3SiCH_2CH_2CH_2NMe_2nBu]^+$ $BF_4^-$
No. 27 $[Ph_3SiCH_2CH_2CH_2NMe_2nBu]^+$ $ClO_4^-$
No. 28 $[Ph_3SiCH_2CH_2CH_2NMe_2Benz]^+$ $ClO_4^-$
No. 29 $[Ph_3SiCH_2CH_2CH_2NMe_2Et]^+$ $SbCl_5^-$
No. 30 $[Ph_3SiCH_2CH_2CH_2NMe_2nHex]^+$ $SbCl_5^-$
No. 31 $[Ph_2MeSiCH_2CH_2CH_2NMe_3]^+$ $I^-$
No. 32 $[Ph_2MeSiCH_2CH_2CH_2NMe_3]^+$ $Br^-$
No. 33 $[Ph_2MeSiCH_2CH_2CH_2NMe_2Et]^+$ $I^-$
No. 34 $[Ph_2MeSiCH_2CH_2CH_2NMe_2nPr]^+$ $I^-$
No. 35 $[Ph_2MeSiCH_2CH_2CH_2NMe_2nBu]^+$ $I^-$
No. 36 $[Ph_2MeSiCH_2CH_2CH_2NMe_2nBu]^+$ $Br^-$
No. 37 $[Ph_2MeSiCH_2CH_2CH_2NMe_2nHex]^+$ $I^-$
No. 38 $[Ph_2MeSiCH_2CH_2CH_2NMe_2cHex]^+$ $I^-$
No. 39 $[Ph_2MeSiCH_2CH_2CH_2NMe_2Benz]^+$ $I^-$
  (Benz=$CH_2Ph$)
No. 40 $[Ph_2MeSiCH_2CH_2CH_2NMe_2Benz]^+$ $Br^-$
No. 41 $[Ph_2MeSiCH_2CH_2CH_2NMe_2nPr]^+$ $I^-$

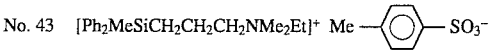

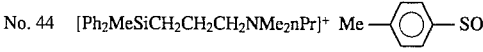

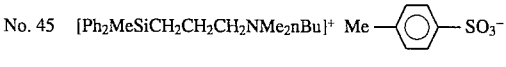

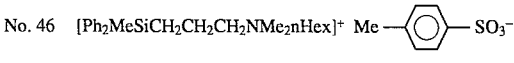

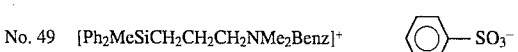

No. 50 [Ph₂MeSiCH₂CH₂CH₂NMe₂Et]⁺ 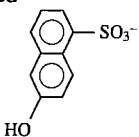

No. 51 [Ph₂MeSiCH₂CH₂CH₂NMe₂nPr]⁺ ⟨naphthalene⟩-SO₃⁻ with OH

No. 52 [Ph₂MeSiCH₂CH₂CH₂NMe₂Benz]⁺ ⟨naphthalene⟩-SO₃⁻ with HO

No. 53 [Ph₂MeSiCH₂CH₂CH₂NMe₃]⁺ BPh₄⁻
No. 54 [Ph₂MeSiCH₂CH₂CH₂NMe₂nBu]⁺ BPh₄⁻
No. 55 [Ph₂MeSiCH₂CH₂CH₂NMe₂Et]⁺ BF₄⁻
No. 56 [Ph₂MeSiCH₂CH₂CH₂NMe₂nBu]⁺ BF₄⁻
No. 57 [Ph₂MeSiCH₂CH₂CH₂NMe₂nBu]⁺ ClO₄⁻
No. 58 [Ph₂MeSiCH₂CH₂CH₂NMe₂Benz]⁺ ClO₄⁻
No. 59 [Ph₂MeSiCH₂CH₂CH₂NMe₂Et]⁺ SbCl₅⁻
No. 60 [Ph₂MeSiCH₂CH₂CH₂NMe₂nHex]⁺ SbCl₅⁻
No. 61 [Me₂PhSiCH₂CH₂CH₂NMe₃]⁺ I⁻
No. 62 [Me₂PhSiCH₂CH₂CH₂NMe₃]⁺ Br⁻
No. 63 [Me₂PhSiCH₂CH₂CH₂NMe₂Et]⁺ I⁻
No. 64 [Me₂PhSiCH₂CH₂CH₂NMe₂nPr]⁺ I⁻
No. 65 [Me₂PhSiCH₂CH₂CH₂NMe₂nBu]⁺ I³¹
No. 66 [Me₂PhSiCH₂CH₂CH₂NMe₂nBu]⁺ Br⁻
No. 67 [Me₂PhSiCH₂CH₂CH₂NMe₂nHex]⁺ I⁻
No. 68 [Me₂PhSiCH₂CH₂CH₂NMe₂cHex]⁺ I⁻
No. 69 [Me₂PhSiCH₂CH₂CH₂NMe₂Benz]⁺ I⁻
(Benz=CH₂Ph)
No. 70 [Me₂PhSiCH₂CH₂CH₂NMe₂Benz]⁺ Br⁻
No. 71 [Me₂PhSiCH₂CH₂CH₂NMe₂nPr]⁺ I⁻

No. 72 [Me₂PhSiCH₂CH₂CH₂NMe₃]⁺ Me—⟨C₆H₄⟩—SO₃⁻

No. 73 [Me₂PhSiCH₂CH₂CH₂NMe₂Et]⁺ Me—⟨C₆H₄⟩—SO₃⁻

No. 74 [Me₂PhSiCH₂CH₂CH₂NMe₂nPr]⁺ Me—⟨C₆H₄⟩—SO₃⁻

No. 75 [Me₂PhSiCH₂CH₂CH₂NMe₂nBu]⁺ Me—⟨C₆H₄⟩—SO₃⁻

No. 76 [Me₂PhSiCH₂CH₂CH₂NMe₂nHex]⁺ Me—⟨C₆H₄⟩—SO₃⁻

No. 77 [Me₂PhSiCH₂CH₂CH₂NMe₃]⁺ HO—⟨naphthalene⟩—SO₃⁻

No. 78 [Me₂PhSiCH₂CH₂CH₂NMe₂Et]⁺ HO—⟨naphthalene⟩—SO₃⁻

No. 79 [Me₂PhSiCH₂CH₂CH₂NMe₂Benz]⁺ HO—⟨naphthalene⟩—SO₃⁻

No. 80 [Me₂PhSiCH₂CH₂CH₂NMe₂Et]⁺ 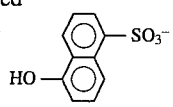

No. 81 [Me₂PhSiCH₂CH₂CH₂NMe₂nPr]⁺ ⟨naphthalene with HO, HO⟩—SO₃⁻

No. 82 [Me₂PhSiCH₂CH₂CH₂NMe₂Benz]⁺ HO—⟨naphthalene⟩—SO₃⁻ with HO

No. 83 [Me₂PhSiCH₂CH₂CH₂NMe₃]⁺ BPh₄⁻
No. 84 [Me₂PhSiCH₂CH₂CH₂NMe₂nBu]⁺ BPh₄⁻
No. 85 [Me₂PhSiCH₂CH₂CH₂NMe₂Et]⁺ BF₄⁻
No. 86 [Me₂PhSiCH₂CH₂CH₂NMe₂nBu]⁺ BF₄⁻
No. 87 [Me₂PhSiCH₂CH₂CH₂NMe₂nBu]⁺ ClO₄⁻
No. 88 [Me₂PhSiCH₂CH₂CH₂NMe₂Benz]⁺ ClO₄⁻
No. 89 [Me₂PhSiCH₂CH₂CH₂NMe₂Et]⁺ SbCl₅⁻
No. 90 [Me₂PhSiCH₂CH₂CH₂NMe₂nHex]⁺ SbCl₅⁻
No. 91 [Me₃SiCH₂CH₂CH₂NMe₃]⁺ I⁻
No. 92 [Me₃SiCH₂CH₂CH₂NMe₃]⁺ Br⁻
No. 93 [Me₃SiCH₂CH₂CH₂NMe₂Et]⁺ I⁻
No. 94 [Me₃SiCH₂CH₂CH₂NMe₂nPr]⁺ I⁻
No. 95 [Me₃SiCH₂CH₂CH₂NMe₂nBu]⁺ I⁻
No. 96 [Me₃SiCH₂CH₂CH₂NMe₂NBu]⁺ Br⁻
No. 97 [Me₃SiCH₂CH₂CH₂NMe₂nHex]⁺ I⁻
No. 98 [Me₃SiCH₂CH₂CH₂NMe₂cHex]⁺ I⁻
No. 99 [Me₃SiCH₂CH₂CH₂NMe₂Benz]⁺ I⁻
(Benz=CH₂Ph)
No. 100 [Me₃SiCH₂CH₂CH₂NMe₂Benz]⁺ Br⁻
No. 101 [Me₃SiCH₂CH₂CH₂NMe₂nPr]⁺ I⁻

No. 102 [Me₃SiCH₂CH₂CH₂NMe₃]⁺ Me—⟨C₆H₄⟩—SO₃⁻

No. 103 [Me₃SiCH₂CH₂CH₂NMe₂Et]⁺ Me—⟨C₆H₄⟩—SO₃⁻

No. 104 [Me₃SiCH₂CH₂CH₂NMe₂nPr]⁺ Me—⟨C₆H₄⟩—SO₃⁻

No. 105 [Me₃SiCH₂CH₂CH₂NMe₂nBu]⁺ Me—⟨C₆H₄⟩—SO₃⁻

No. 106 [Me₃SiCH₂CH₂CH₂NMe₂nHex]⁺ Me—⟨C₆H₄⟩—SO₃⁻

No. 107 [Me₃SiCH₂CH₂CH₂NMe₃]⁺ HO—⟨naphthalene⟩—SO₃⁻

No. 108 [Me₃SiCH₂CH₂CH₂NMe₂Et]⁺ HO—⟨naphthalene⟩—SO₃⁻

No. 109 [Me₃SiCH₂CH₂CH₂NMe₂Benz]⁺ HO—⟨naphthalene⟩—SO₃⁻

No. 110 [Me₃SiCH₂CH₂CH₂NMe₂Et]⁺ 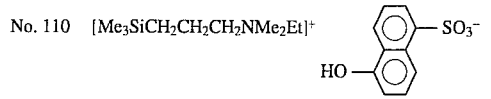

No. 111 [Me₃SiCH₂CH₂CH₂NMe₂nPr]⁺ 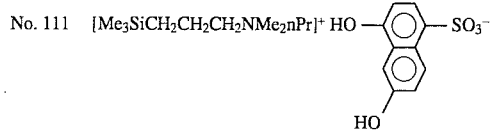

No. 112 [Me₃SiCH₂CH₂CH₂NMe₂Benz]⁺ 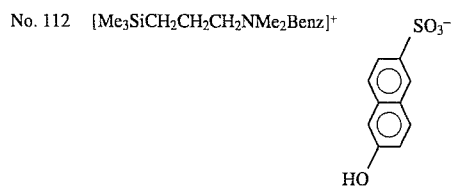

No. 113 [Me₃SiCH₂CH₂CH₂NMe₃]⁺ BPh₄⁻
No. 114 [Me₃SiCH₂CH₂CH₂NMe₂nBu]⁺ BPh₄⁻
No. 115 [Me₃SiCH₂CH₂CH₂NMe₂Et]⁺ BF₄⁻
No. 116 [Me₃SiCH₂CH₂CH₂NMe₂nBu]⁺ BF₄⁻
No. 117 [Me₃SiCH₂CH₂CH₂NMe₂nBu]⁺ ClO₄⁻
No. 118 [Me₃SiCH₂CH₂CH₂NMe₂Benz]⁺ ClO₄⁻
No. 119 [Me₃SiCH₂CH₂CH₂NMe₂Et]⁺ SbCl₅⁻
No. 120 [Me₃SiCH₂CH₂CH₂NMe₂nHex]⁺ SbCl₅⁻

No. 121

No. 122

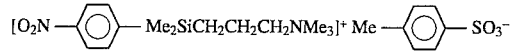

No. 123

No. 124

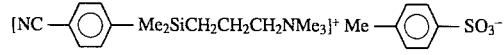

No. 125

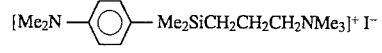

No. 126

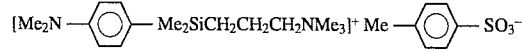

No. 127

[Me₂nBuSiCH₂CH₂CH₂NMe₃]⁺ I⁻

No. 128

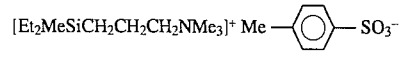

No. 129

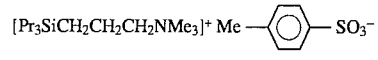

No. 130

[MeEtPhSiCH₂CH₂CH₂NMe₂Et]⁺ I⁻

Of the above-mentioned organosilicon compounds of formula (I), particularly preferable examples are as follows:
(1) All of $R^1$, $R^2$ and $R^3$ represent an unsubstituted phenyl group.
(2) One of $R^1$, $R^2$ and $R^3$ represents an unsubstituted phenyl group, and the other two represent an alkyl group having 1 to 6 carbon atoms.
(3) Two of $R^1$, $R^2$ and $R^3$ represent an unsubstituted phenyl group, and the other one represents an alkyl group having 1 to 6 carbon atoms.
(4) All of $R^1$, $R^2$ and $R^3$ represent an alkyl group having 1 to 6 carbon atoms.

In the above-mentioned preferable examples (2) to (4), when the alkyl group is methyl group, further preferable results can be obtained.

According to the present invention, there is provided a toner for developing latent electrostatic images comprising toner particles which comprise a resin, a coloring agent, and the previously mentioned organosilicon compound of formula (I).

Examples of the resin for use in the toner of the present invention include polystyrene resin, acrylic resin, styrene—methacrylate copolymer and epoxy resin.

As the coloring agent for use in the toner of the present invention, commercially available C.I. Pigment Yellow 142, "Kayaset Yellow E-L2 R" made by Nippon Kayaku Co., Ltd.; commercially available C.I. Solvent Red 179, "Kayaset Red A-G" made by Nippon Kayaku Co., Ltd.; commercially available C.I. Solvent Blue 105, "Kayaset Blue FR" made by Nippon Kayaku Co., Ltd.; and carbon black can be employed. The coloring agent for use in the present invention is not limited to the above-mentioned products.

It is preferable that the amount of the organosilicon compound of formula (I) be in a range of 0.5 to 30 parts by weight, more preferably in a range of 1 to 10 parts by weight, to 100 parts by weight of the resin in the toner. When the organosilicon compound of the present invention is contained in the toner within the above-mentioned range, the toner can acquire a proper charge quantity.

The toner of the present invention may further comprise a variety of additives, for instance, an image-fixing promoting agent such as polypropylene, polyethylene or carnauba wax; a fluidity-improving agent such as hydrophobic silica, alumina, molybdenum sulfide or titanium oxide; and a cleaning performance improving agent such as zinc stearate, magnesium stearate or zinc laurate.

A two-component developer of the present invention comprises the previously mentioned toner which comprises toner particles comprising the resin, the coloring agent and the organosilicon compound of formula (I), and a carrier.

As the carrier component for use in the developer of the present invention, magnetic materials such as iron, nickel, cobalt, and ferrite are preferably employed.

The toner of the present invention can be prepared in such a manner that the previously mentioned resin, coloring agent, and organosilicon compound of formula (I) serving as a charge controlling agent are melted and kneaded in an apparatus capable of mixing the materials by the application of heat thereto, such as a kneader or a two-roll mill, and the mixture thus obtained is then cooled to set and pulverized in a jet-mill or ball mill until the average particle diameter of the ground particles reaches 1 to 50 μm. Alternatively, the resin is dissolved in a solvent to prepare a resin solution, and the organosilicon compound of formula (I) is added to the resin solution with stirring. The thus obtained mixture is

SYNTHESIS EXAMPLE 1

[Synthesis of 3-N,N-dimethylaminopropyl triphenylsilane]

13.00 g (0.05 mol) of triphenylsilane was dissolved in 35 ml of isopropyl alcohol. To this solution, 0.01 g (0.00001 mol) of chloroplatinic acid.2hydrate was added. Thereafter, a solution prepared by dissolving 4.28 g (0.05 mol) of N,N-dimethylaminoallylamine in 5 ml of isopropyl alcohol was added dropwise to the above mixture at room temperature.

The reaction mixture thus obtained was refluxed for 6 hours by the application of heat thereto. After the reaction mixture was cooled to room temperature, the solvent was distilled away from the reaction mixture and the residue was distilled under reduced pressure. Thus, 12.80 g of 3-N,N-dimethylaminopropyl triphenylsilane was obtained in a yield 74.1%.

It was possible to obtain this compound likewise by subjection the residue to silica gel chromatography using chloroform as an eluting solution and recrystallizing the obtained material from ethanol after the solvent was distilled away.

The melting point of 3-N,N-dimethylaminopropyl triphenylsilane was 38.5° to 39.0° C., and the boiling point thereof was 133.0° to 136.0° C. (2 Torr).

The results of the elemental analysis of the above-mentioned compound were as follows:

|  | % C | % H | % N |
|---|---|---|---|
| Calculated | 79.94 | 7.88 | 4.05 |
| Found | 79.87 | 7.87 | 3.94 |

SYNTHESIS EXAMPLE 2

[Synthesis of 3-N,N-dimethylaminopropyl diphenylmethylsilane]

25.00 g (0.126 mol) of diphenylmethylsilane was dissolved in 150 ml of isopropyl alcohol. To this solution, 0.01 g (0.00001 mol) of chloroplatinic acid.2hydrate was added. Thereafter, a solution prepared by dissolving 11.00 g (0.129 mol) of N,N-dimethylaminoallylamine in 10 ml of isopropyl alcohol was added dropwise to the above mixture at room temperature.

The reaction mixture thus obtained was refluxed for 8 hours by the application of heat thereto. After the reaction mixture was cooled to room temperature, the solvent was distilled away from the reaction mixture and the residue was distilled under reduced pressure. Thus, 26.15 g of 3-N,N-dimethylaminopropyl diphenylmethylsilane was obtained in a yield 73.2%.

The boiling point of 3-N,N-dimethylaminopropyl diphenylmethylsilane was 90.0° to 93.0° C. (2 Torr).

The results of the elemental analysis of the above-mentioned compound were as follows:

|  | % C | % H | % N |
|---|---|---|---|
| Calculated | 76.26 | 8.89 | 4.94 |
| Found | 75.83 | 8.75 | 4.55 |

SYNTHESIS EXAMPLE 3

[Synthesis of 3-N,N-dimethylaminopropyl dimethylphenylsilane]

25.00 g (0.126 mol) of dimethylphenylsilane was dissolved in 150 ml of isopropyl alcohol. To this solution, 0.01 g (0.00001 mol) of chloroplatinic acid.2hydrate was added. Thereafter, a solution prepared by dissolving 11.00 g (0.129 mol) of N,N-dimethylaminoallylamine in 10 ml of isopropyl alcohol was added dropwise to the above mixture at room temperature.

The reaction mixture thus obtained was refluxed for 8 hours by the application of heat thereto. After the reaction mixture was cooled to room temperature, the solvent was distilled away from the reaction mixture and the residue was distilled under reduced pressure. Thus, 26.15 g of 3-N,N-dimethylaminopropyl dimethylphenylsilane was obtained in a yield 73.2%.

The boiling point of 3-N,N-dimethylaminopropyl dimethylphenylsilane was 60.0° to 64.0° C. (2 Torr).

The results of the elemental analysis of the above-mentioned compound were as follows:

|  | % C | % H | % N |
|---|---|---|---|
| Calculated | 76.26 | 8.89 | 4.94 |
| Found | 75.83 | 8.75 | 4.55 |

SYNTHESIS EXAMPLE 4

[Synthesis of 3-N,N-dimethylaminopropyl trimethylsilane]

7.00 g (0.288 mol) of magnesium and 50 ml of tetrahydrofuran were placed in a 500-ml three-necked flask, and the atmosphere was replaced with argon. As a solution prepared by dissolving 24.33 g (0.200 mol) of 3-N,N-dimethylaminopropyl chloride in 30 ml of tetrahydrofuran was added to the above-mentioned mixture through a dropping funnel little by little, the reaction was initiated.

After the completion of addition, 100 ml of tetrahydrofuran was further added to the reaction mixture, and the reaction mixture was refluxed for 2 hours. Thus, a Grignard reagent was obtained.

A solution prepared by dissolving 21.70 g (0.200 mol) of trimethylchlorosilane in 25 ml of tetrahydrofuran was slowly added to the above obtained Grignard reagent at room temperature. The reaction mixture thus obtained was refluxed for 6 hours under application of heat thereto. Thereafter, the reaction mixture was stirred at room temperature for twenty-four hours.

Before going further in the description of exemplary embodiments, it should be noted that similar parts are denoted by like reference numerals throughout this application.

poured into water, and a resulting precipitate is obtained by filtration and dried. With the addition of the coloring agent, the thus obtained mixture is kneaded under application of heat, and pulverized so as to obtain the particles with an average particle diameter ranging from 1 to 50 μm.

Other features of this invention will become apparent in the course of the following description of exemplary embodiments, which are given for illustration of the invention and are not intended to be limiting thereof.

13

Then, an aqueous solution of ammonium chloride was added to the reaction mixture to decompose an inorganic salt, and the reaction mixture was extracted with ether. The ether solution thus obtained was dried over anhydrous magnesium sulfate. Then, the solvent was distilled away and the residue was distilled under reduced pressure. Thus, 20.40 g of 3-N,N-dimethylaminopropyl trimethylsilane was obtained in a yield 64.0%.

The boiling point of 3-N,N-dimethylaminopropyl trimethylsilane was 74.0° to 76.0° C. (54 Torr).

The results of the elemental analysis of the above-mentioned compound were as follows:

|  | % C | % H | % N |
|---|---|---|---|
| Calculated | 60.30 | 13.28 | 8.79 |
| Found | 60.87 | 13.11 | 9.08 |

SYNTHESIS EXAMPLE 5

[Preparation of Organosilicon Compound No. 1]

3.45 g (0.01 mol) of 3-N,N-dimethylaminopropyl triphenylsilane synthesized in Synthesis Example 1 was dissolved in 50 ml of dry acetone. To the thus obtained mixture, a solution prepared by dissolving 1.42 g (0.01 mol) of methyl iodide in 2 ml of acetone was added dropwise at room temperature.

After the reaction mixture was stirred at room temperature for 8 hours, the resulting crystals were obtained by filtration. The crystals thus obtained were successively washed with 50 ml of dry acetone, and 50 ml of dry ether, and dried at 80° C. under reduced pressure for 6 hours. Thus, 5.79 g of organosilicon compound No. 1 was obtained in the form of white crystals. The yield was 99.0%.

SYNTHESIS EXAMPLE 6

[Preparation of Organosilicon Compound No. 31]

3.40 g (0.012 mol) of 3-N,N-dimethylaminopropyl diphenylmethylsilane synthesized in Synthesis Example 2 was dissolved in 50 ml of dry acetone. To the thus obtained mixture, a solution prepared by dissolving 1.72 g (0.012 mol) of methyl iodide in 2 ml of acetone was added dropwise at room temperature.

After the reaction mixture was stirred at room temperature for 8 hours, the resulting crystals were obtained by filtration. The crystals thus obtained were successively washed with 50 ml of dry acetone, and 50 ml of dry ether, and dried at 80° C. under reduced pressure for 6 hours. Thus, 3.97 g of organosilicon compound No. 31 was obtained in the form of white crystals. The yield was 77.8%.

SYNTHESIS EXAMPLE 7

[Preparation of Organosilicon Compound No. 61]

3.32 g (0.015 mol) of 3-N,N-dimethylaminopropyl dimethylphenylsilane synthesized in Synthesis Example 3 was dissolved in 50 ml of dry acetone. To the thus obtained mixture, a solution prepared by dissolving 2.13 g (0.015 mol) of methyl iodide in 2 ml of acetone was added dropwise at room temperature.

14

After the reaction mixture was stirred at room temperature for 8 hours, the resulting crystals were obtained by filtration. The crystals thus obtained were successively washed with 50 ml of dry acetone, and 50 ml of dry ether, and dried at 80° C. under reduced pressure for 6 hours. Thus, 4.59 g of organosilicon compound No. 61 was obtained in the form of white crystals. The yield was 84.2%.

SYNTHESIS EXAMPLE 8

[Preparation of Organosilicon Compound No. 91]

3.19 g (0.02 mol) of 3-N,N-dimethylaminopropyl trimethylsilane synthesized in Synthesis Example 4 was dissolved in 50 ml of dry tetrahydrofuran. To the thus obtained mixture, a solution prepared by dissolving 2.85 g (0.02 mol) of methyl iodide in 2 ml of tetrahydrofuran was added dropwise at room temperature.

After the reaction mixture was stirred at room temperature for 6 hours, the resulting crystals were obtained by filtration. The crystals thus obtained were washed with 50 ml of dry ether, and dried at 80° C. under reduced pressure for 6 hours. Thus, 5.43 g of organosilicon compound No. 91 was obtained in the form of white crystals. The yield was 90.0%.

SYNTHESIS EXAMPLES 9 TO 41

The procedure for preparation of the organosilicon compound in Synthesis Example 5, 6, 7 or 8 was repeated except that the corresponding 3-N,N-dimethylaminopropyl silane compound and quaternarization agent were employed, so that organosilicon compounds of the present invention as shown in Table 1 were obtained.

The yield, the melting point, and the decomposition point of each organosilicon compound are shown in Table 1; and the results of the elemental analysis of each organosilicon compound are shown in Table 2.

TABLE 1

| Synthesis Example No. | Compound No. | Yield (%) | Melting Point (°C.) | Decomposition Point (°C.) |
|---|---|---|---|---|
| 5 | 1 | 99.0 | — | 260.0 |
| 9 | 3 | 96.7 | — | 242.8 |
| 10 | 4 | 75.7 | 179.2 | 217.7 |
| 11 | 5 | 41.2 | 176.8 | 220.7 |
| 12 | 6 | 41.0 | — | 216.3 |
| 13 | 12 | 80.0 | 216.4 | 290.3 |
| 14 | 13 | 25.7 | 187.3 | 278.6 |
| 15 | 15 | 32.6 | 197.8 | 275.0 |
| 16 | 16 | 19.0 | 155.9 | 271.6 |
| 17 | 24 | 38.6 | — | 280.8 |
| 6 | 31 | 77.8 | 151.3 | 234.4 |
| 18 | 33 | 90.3 | — | 218.2 |
| 19 | 34 | 86.4 | 121.0 | 206.8 |
| 20 | 35 | 48.3 | — | 210.5 |
| 21 | 42 | 66.7 | 145.4 | 281.5 |
| 22 | 43 | 56.0 | 102.4 | 273.5 |
| 23 | 45 | 51.0 | 84.9 | 276.3 |
| 24 | 46 | 24.8 | 97.7 | 266.7 |
| 25 | 54 | 29.7 | — | 256.5 |
| 7 | 61 | 84.2 | 122.2 | 221.1 |
| 26 | 63 | 63.3 | 125.6 | 218.2 |
| 27 | 64 | 38.3 | 125.7 | 212.1 |
| 28 | 65 | 58.1 | 65.2 | 207.4 |
| 29 | 72 | 77.8 | 137.3 | 276.9 |
| 30 | 73 | 75.6 | 88.4 | 260.9 |
| 31 | 75 | 73.9 | 90.3 | 260.9 |
| 32 | 76 | 28.6 | 78.3 | 263.2 |
| 33 | 84 | 30.4 | 152.4 | 330.5 |
| 8 | 91 | 90.0 | 121.0 | 225.8 |
| 34 | 93 | 92.2 | 110.5 | 219.1 |
| 35 | 94 | 87.2 | 122.2 | 204.7 |

TABLE 1-continued

| Synthesis Example No. | Compound No. | Yield (%) | Melting Point (°C.) | Decomposition Point (°C.) |
|---|---|---|---|---|
| 36 | 95 | 85.6 | 89.6 | 203.4 |
| 37 | 102 | 91.1 | 171.5 | 278.0 |
| 38 | 103 | 55.1 | 133.8 | 269.0 |
| 39 | 105 | 45.8 | 135.0 | 262.3 |
| 40 | 106 | 44.6 | 79.1 | 262.5 |
| 41 | 114 | 35.5 | — | 157.0 |

TABLE 2

| Synthesis Example No. | Compound No. | Elemental Analysis (Calculated) Found | | |
|---|---|---|---|---|
| | | % C | % H | % N |
| 5 | 1 | (59.13) / 59.01 | (6.85) / 6.37 | (2.87) / 2.35 |
| 9 | 3 | (59.87) / 59.63 | (6.43) / 6.63 | (2.79) / 2.42 |
| 10 | 4 | (60.57) / 60.61 | (6.64) / 6.84 | (2.71) / 2.55 |
| 11 | 5 | (61.23) / 61.00 | (6.85) / 7.04 | (2.64) / 2.28 |
| 12 | 6 | (67.20) / 67.15 | (7.51) / 7.88 | (2.90) / 2.80 |
| 13 | 12 | (70.01) / 70.01 | (7.01) / 7.22 | (2.63) / 2.44 |
| 14 | 13 | (70.41) / 70.43 | (7.20) / 7.48 | (2.56) / 2.42 |
| 15 | 15 | (71.16) / 71.29 | (7.55) / 7.89 | (2.44) / 2.28 |
| 16 | 16 | (71.83) / 71.84 | (7.87) / 8.20 | (2.32) / 2.10 |
| 17 | 24 | (84.85) / 84.78 | (7.82) / 7.88 | (1.94) / 1.77 |
| 6 | 31 | (53.64) / 53.56 | (6.63) / 7.00 | (3.29) / 2.89 |
| 18 | 33 | (54.66) / 54.41 | (6.88) / 7.20 | (3.18) / 2.90 |
| 19 | 34 | (55.62) / 55.28 | (7.11) / 7.45 | (3.08) / 3.18 |
| 20 | 35 | (56.52) / 56.34 | (7.33) / 7.59 | (3.00) / 3.06 |
| 21 | 42 | (66.48) / 66.18 | (7.51) / 7.90 | (2.98) / 2.99 |
| 22 | 43 | (67.03) / 67.25 | (7.705) / 8.01 | (2.89) / 2.95 |
| 23 | 45 | (68.05) / 68.43 | (8.07) / 8.21 | (2.73) / 2.70 |
| 24 | 46 | (68.97) / 68.73 | (8.40) / 8.70 | (2.59) / 2.66 |
| 25 | 54 | (83.79) / 83.71 | (8.25) / 8.63 | (2.12) / 2.15 |
| 7 | 61 | (46.28) / 45.91 | (7.21) / 7.59 | (3.85) / 3.96 |
| 26 | 63 | (47.74) / 47.60 | (7.48) / 7.80 | (3.71) / 3.48 |
| 27 | 64 | (49.10) / 48.89 | (7.73) / 7.85 | (3.58) / 3.52 |
| 28 | 65 | (50.36) / 50.31 | (7.96) / 7.71 | (3.45) / 3.39 |
| 29 | 72 | (61.87) / 61.74 | (8.16) / 8.53 | (3.44) / 3.57 |
| 30 | 73 | (62.67) / 62.33 | (8.37) / 8.61 | (3.32) / 3.66 |
| 31 | 75 | (64.85) / 64.49 | (8.74) / 9.14 | (3.11) / 3.31 |
| 32 | 76 | (65.36) / 64.98 | (9.07) / 9.11 | (3.93) / 3.25 |
| 33 | 84 | (82.38) / 82.04 | (8.77) / 8.89 | (3.34) / 3.55 |
| 8 | 91 | (35.88) / 35.74 | (8.03) / 8.25 | (4.65) / 4.45 |
| 34 | 93 | (38.09) / 38.22 | (8.31) / 8.53 | (4.44) / 4.42 |
| 35 | 94 | (40.11) / 39.90 | (8.57) / 8.69 | (4.25) / 4.30 |
| 36 | 95 | (41.98) / 62.05 | (8.81) / 8.68 | (4.08) / 4.34 |
| 37 | 102 | (54.51) / 54.55 | (8.54) / 8.62 | (4.24) / 4.18 |
| 38 | 103 | (55.77) / 55.82 | (8.78) / 8.68 | (4.06) / 4.25 |
| 39 | 105 | (58.87) / 58.67 | (9.62) / 9.89 | (3.61) / 3.59 |
| 40 | 106 | (60.67) / 60.52 | (9.94) / 9.78 | (3.37) / 3.48 |
| 41 | 114 | (80.72) / 80.48 | (9.41) / 9.73 | (2.61) / 2.77 |

EXAMPLE 1

[Preparation of Toner No. 1]

The following components were thoroughly mixed and kneaded in a hot mill, and pulverized and classified, so that toner particles with an average particle diameter of 8.0 μm were obtained:

| | Parts by Weight |
|---|---|
| Styrene-methacrylate resin | 100 |
| Organosilicon compound No. 1 | 5 |
| Carbon black | 10 |

[Preparation of Developer No. 1]

The above prepared toner No. 1 of the present invention was mixed with commercially available iron carrier particles, "EFV200-300" (Trademark), made by Nihon Teppun Co., Ltd, and the mixture thus obtained was thoroughly stirred, so that a two-component dry developer No. 1 according to the present invention having a toner concentration of 7% was obtained.

EXAMPLES 2 TO 13

The procedure for preparation of the two-component dry developer No. 1 in Example 1 was repeated except that the formulation for the toner No. 1 was changed to each formulation as shown in Table 3, whereby two-component dry developers No. 2 to No. 13 according to the present invention were obtained.

TABLE 3

| | Toner Formulation | | |
|---|---|---|---|
| | Resin (parts by weight) | Organosilicon compound No. (parts by weight) | Coloring agent (parts by weight) |
| Ex. 2 | polyester resin (100) | No. 5 (8) | carbon black (10) |
| Ex. 3 | epoxy resin (100) | No. 12 (10) | carbon black (10) |
| Ex. 4 | styrene-methacrylate resin (100) | No. 15 (5) | carbon black (10) |
| Ex. 5 | styrene-methacrylate resin (100) | No. 31 (5) | carbon black (10) |
| Ex. 6 | polyester resin (100) | No. 34 (6) | carbon black (10) |
| Ex. 7 | epoxy resin (100) | No. 42 (10) | carbon black (10) |
| Ex. 8 | styrene-methacrylate resin (100) | No. 61 (5) | carbon black (10) |
| Ex. 9 | polyester resin (100) | No. 63 (8) | carbon black (10) |
| Ex. 10 | epoxy resin (100) | No. 72 (10) | carbon black (10) |
| Ex. 11 | styrene-methacrylate resin (100) | No. 91 (5) | carbon black (10) |
| Ex. 12 | polyester resin (100) | No. 102 (10) | carbon black (10) |
| Ex. 13 | epoxy resin (100) | No. 105 (10) | carbon black (10) |

COMPARATIVE EXAMPLE 1

The procedure for preparation of the two-component dry developer No. 1 in Example 1 was repeated except that the formulation for the toner No. 1 of the present invention was changed to the following formulation for a comparative toner No. 1:

| | Parts by Weight |
|---|---|
| Styrene-methacrylate resin | 100 |
| Quaternary ammonium salt compound "Bontron P-51" (Trademark), made by Orient Chemical industries, Ltd. | 5 |
| Carbon black | 10 |

[Preparation of Comparative Developer No. 1]

The above prepared comparative toner No. 1 was mixed with commercially available iron carrier particles, "EFV200-300" (Trademark), made by Nihon Teppun Co., Ltd, and the mixture thus obtained was thoroughly stirred, so that a comparative two-component dry developer No. 1 having a toner concentration of 7% was obtained.

Using the above prepared two-component dry developers Nos. 1 to 13 according to the present invention and comparative two-component dry developer No. 1, the following items were evaluated. The results are shown in Table 4.

(1) Durability of Toner

Each of the above prepared two-component dry developers was supplied to a commercially available electrophotographic copying machine "FT4060" (Trademark), made by Ricoh Company, Ltd., and copies were continuously made. The charge quantity of the toner was measured by the blow-off method at the initial stage and after 20,000 copies were made. In addition, the image quality of copied images was observed after making of 20,000 copies.

(2) Environmental Stability of Toner

Before mixing the toner particles and the carrier particles to prepare a two-component dry developer, the toner particles and the carrier particles were allowed to stand in an atmosphere of 30° C. and 90% RH for 2 hours. The charge quantity of the toner at a high humidity was measured after those particles were mixed and stirred to obtain a developer. Similarly, the charge quantity of the toner at a low humidity was measured after the toner particles and the carrier particles were allowed to stand in an atmosphere of 10° C. and 30% RH for 2 hours. Then, the degree of variability in the charge quantity of toner was obtained in accordance with the following formula:

$$\text{Degree of Variability} = \left(1 - \frac{\text{Charge qty. at high humidity}}{\text{Charge qty. at low humidity}}\right) \times 100$$

TABLE 4

| | Durability of Toner | | | Environmental Stability of Toner Charge quantity of toner (μC/gr) | | |
|---|---|---|---|---|---|---|
| | Charge quantity of toner (μC/gr) | | | | | |
| Example No. | Initial stage | After making of copies | Image quality after making of copies | High humidity | Low humidity | Degree of variability |
| Ex. 1 | 25.3 | 24.8 | clear | 25.6 | 29.5 | 13% |
| Ex. 2 | 27.1 | 25.3 | clear | 24.5 | 31.4 | 22% |
| Ex. 3 | 33.5 | 34.3 | clear | 33.5 | 35.2 | 5% |
| Ex. 4 | 41.6 | 43.8 | clear | 39.5 | 42.1 | 6% |
| Ex. 5 | 23.5 | 25.5 | clear | 24.7 | 28.1 | 14% |
| Ex. 6 | 34.1 | 36.4 | clear | 32.3 | 37.6 | 16% |
| Ex. 7 | 28.9 | 29.8 | clear | 28.6 | 30.3 | 6% |
| Ex. 8 | 22.1 | 24.6 | clear | 22.7 | 26.5 | 16% |
| Ex. 9 | 17.3 | 20.6 | clear | 18.5 | 21.6 | 17% |
| Ex. 10 | 27.6 | 28.9 | clear | 29.2 | 32.2 | 11% |
| Ex. 11 | 32.4 | 34.9 | clear | 33.7 | 35.1 | 4% |
| Ex. 12 | 36.8 | 37.5 | clear | 34.0 | 38.3 | 12% |
| Ex. 13 | 30.0 | 32.2 | clear | 31.3 | 33.6 | 6% |
| Comp. Ex. 1 | 24.2 | 10.9 (*) | not clear (**) | 10.8 | 25.6 | 58% |

(*) This value was obtained after making of 10,000 copies.
(**) Toner deposition on background considerably occurred.

As previously mentioned, the organosilicon compound according to the present invention, which is a novel compound, is found to be superior in the thermal stability. The moisture absorption of the organosilicon compound in the form of a quaternary salt according to the present invention is remarkably low as compared with the corresponding carbon compound in the form of a quaternary salt.

Such an organosilicon compound of formula (I) can be easily produced by converting 3-N,N-dimethylaminopropyl silane to a quaternary salt by use of a quaternization agent.

The toner for developing latent electrostatic images according to the present invention comprises the previously mentioned organosilicon compound, so that the variation in the charge quantities depending on the environmental conditions can be minimized, and the image quality of the obtained images does not deteriorate after the copies are repeatedly made. Furthermore, the compatibility of the organosilicon compound of formula (I) with the resin is so good that the toner can be easily prepared.

In addition, since the organosilicon compound of the present invention is colorless, it can be applied to a color toner.

What is claimed is:

1. A toner for developing latent electrostatic images comprising toner particles which comprise a resin, a coloring agent, and an organosilicon compound of formula (I):

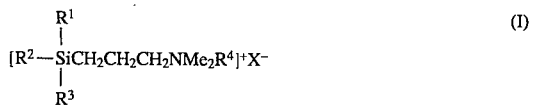

wherein $R^1$, $R^2$ and $R^3$ each is an alkyl group having 1 to 6 carbon atoms, or a phenyl group which may have a substituent; $R^4$ is an alkyl group which may have a substituent, an alicyclic alkyl group, a phenyl group which may have a substituent, or a benzyl group which may have a substituent; and X is a halogen atom, a benzenesulfonate radical, a hydroxynaphthalenesulfonate radical, $BPh_4$, $BF_4$, $ClO_4$, or $SbCl_5$.

2. The toner as claimed in claim 1, wherein said alkyl group represented by $R^1$ to $R^4$ in formula (I) is selected from the group consisting of methyl group, ethyl group, propyl group, butyl group, pentyl group and hexyl group.

3. The toner as claimed in claim 1, wherein said substituent of said phenyl group represented by $R^1$ to $R^3$ in formula (I) is selected from the group consisting of an amino group substituted with at least one alkyl group having 1 to 4 carbon atoms, nitro group, and cyano group.

4. The toner as claimed in claim 1, wherein said substituent of said alkyl group represented by $R^4$ in formula (I) is a halogen atom.

5. The toner as claimed in claim 1, wherein said alicyclic alkyl group represented by $R^4$ in formula (I) is cyclohexyl group.

6. The toner as claimed in claim 1, wherein said substituent of said phenyl group represented by $R^4$ in formula (I) is selected from the group consisting of a halogen atom, an alkyl group having 1 to 4 carbon atoms, and an alkoxyl group having 1 to 4 carbon atoms.

7. The toner as claimed in claim 1, wherein said substituent of said benzyl group represented by $R^4$ in formula (I) is selected from the group consisting of a halogen atom, an alkyl group having 1 to 4 carbon atoms, and an alkoxyl group having 1 to 4 carbon atoms.

8. The toner as claimed in claim 1, wherein said organosilicon compound of formula (I) is contained in an amount ranging from 0.5 to 30 parts by weight to 100 parts by weight of said resin in said toner.

9. The toner as claimed in claim 8, wherein said organosilicon compound of formula (I) is contained in an amount ranging from 1 to 10 parts by weight to 100 parts by weight of said resin in said toner.

10. A two-component dry developer for developing latent electrostatic images comprising:

a toner which comprises toner particles comprising a resin, a coloring agent and an organosilicon compound of formula (I):

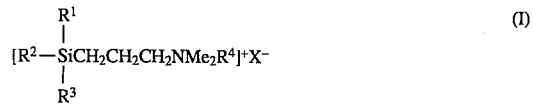

wherein $R^1$, $R^2$ and $R^3$ each is an alkyl group having 1 to 6 carbon atoms, or a phenyl group which may have a substituent; $R^4$ is an alkyl group which may have a substituent, an alicyclic alkyl group, a phenyl group which may have a substituent, or a benzyl group which may have a substituent; and X is a halogen atom, a benzenesulfonate radical, a hydroxynaphthalenesulfonate radical, $BPh_4$, $BF_4$, $ClO_4$, or $SbCl_5$; and a carrier.

11. The two-component dry developer as claimed in claim 10, wherein said alkyl group represented by $R^1$ to $R^4$ in formula (I) is selected from the group consisting of methyl group, ethyl group, propyl group, butyl group, pentyl group and hexyl group.

12. The two-component dry developer as claimed in claim 10, wherein said substituent of said phenyl group represented by $R^1$ to $R^3$ in formula (I) is selected from the group consisting of an amino group substituted with at least one alkyl group having 1 to 4 carbon atoms, nitro group, and cyano group.

13. The two-component dry developer as claimed in claim 10, wherein said substituent of said alkyl group represented by $R^4$ in formula (I) is a halogen atom.

14. The two-component dry developer as claimed in claim 10, wherein said alicyclic alkyl group represented by $R^4$ in formula (I) is cyclohexyl group.

15. The two-component dry developer as claimed in claim 10, wherein said substituent of said phenyl group represented by $R^4$ in formula (I) is selected from the group consisting of a halogen atom, an alkyl group having 1 to 4 carbon atoms, and an alkoxyl group having 1 to 4 carbon atoms.

16. The two-component dry developer as claimed in claim 10, wherein said substituent of said benzyl group represented by $R^4$ in formula (I) is selected from the group consisting of a halogen atom, an alkyl group having 1 to 4 carbon atoms, and an alkoxyl group having 1 to 4 carbon atoms.

17. The two-component dry developer as claimed in claim 10, wherein said organosilicon compound of formula (I) is contained in an amount ranging from 0.5 to 30 parts by weight to 100 parts by weight of said resin in said toner.

18. The two-component dry developer as claimed in claim 17, wherein said organosilicon compound of formula (I) is contained in an amount ranging from 1 to 10 parts by weight to 100 parts by weight of said resin in said toner.

* * * * *